United States Patent [19]
Kilbourn et al.

[11] Patent Number: 5,286,739
[45] Date of Patent: Feb. 15, 1994

[54] PARENTERAL FORMULATIONS FOR THE INHIBITION OF SYSTEMIC HYPOTENSION ASSOCIATED WITH NITRIC OXIDE PRODUCTION OR ENDOTHELIAL DERIVED RELAXING FACTOR

[75] Inventors: Robert G. Kilbourn, Houston, Tex.; Owen W. Griffith; Steven S. Gross, both of New York, N.Y.

[73] Assignee: Board of Regents, University of Texas System, Austin, Tex.

[21] Appl. No.: 767,265

[22] Filed: Sep. 27, 1991

[51] Int. Cl.$^5$ .......................................... A61K 31/195
[52] U.S. Cl. ...................... 514/400; 514/564; 514/565; 514/921; 514/929; 514/561; 514/567; 514/562; 514/419
[58] Field of Search ............... 514/561, 563, 565, 423, 514/567, 562, 419, 400

[56] References Cited

U.S. PATENT DOCUMENTS

| | | | |
|---|---|---|---|
| 3,950,529 | 4/1976 | Fischer et al. | 424/273 |
| 4,859,452 | 8/1989 | Ajani et al. | 424/10 |
| 4,988,724 | 1/1991 | Ajani et al. | 514/399 |
| 5,006,559 | 4/1991 | Askanazi et al. | 514/561 |
| 5,028,627 | 7/1991 | Kilbourn et al. | 514/565 |
| 5,036,052 | 7/1991 | Ozeki et al. | 514/19 |
| 5,059,712 | 10/1991 | Griffith | 562/560 |
| 5,132,453 | 7/1992 | Griffith | 562/560 |
| 5,158,883 | 10/1992 | Griffith | 435/240.2 |
| 5,162,373 | 11/1992 | Ajani et al. | 514/564 |
| 5,189,025 | 2/1993 | Ajani et al. | 514/23 |

FOREIGN PATENT DOCUMENTS

| | | |
|---|---|---|
| 0318446A1 | 5/1989 | European Pat. Off. ...... A61K 37/18 |
| 2516027 | 10/1975 | Fed. Rep. of Germany ......... A61K 31/195 |
| WO91/84023 | 4/1991 | PCT Int'l Appl. |
| 92/08227 | 2/1993 | PCT Int'l Appl. |

OTHER PUBLICATIONS

Moncada et al., "Nitric Oxide: Physiology, Pathophysiology, and Pharmacology," *Pharmacological Reviews*, 43(2):109-142, 1991, published in USA.
Moncada et al., "The L-Arginine: Nitric Oxide Pathway," *Journal of Cardiovascular Pharmacology*, 17(Suppl. 3):S1-S9, 1991, published in USA.
Parratt, J. R., and Stoclet, Jean-Claude, "Possible Role of Nitric Oxide in Refractory Hypotension Associated with Sepsis and Endotoxaemia and with Multiple Organ Failure," *Applied Cardiopulmonary Pathophysiology*, 4:143-149, 1991, published in USA.
Johnston, Jeff, "Molecular Science Sets Its Sights On Septic Shock," *The Journal of NIH Research*, 3:61-65, 1991, published in USA.

(List continued on next page.)

*Primary Examiner*—Frederick E. Waddell
*Assistant Examiner*—T. J. Criares
*Attorney, Agent, or Firm*—Arnold, White & Durkee

[57] ABSTRACT

An anti-hypotensive formulation comprising an essentially arginine-free or low arginine (less than about 0.1%, most preferably, about 0.01%) containing mixture of amino acids is provided. The invention in particular embodiments of the anti-hypotensive formulation includes ornithine, citrulline or both. A method for prophylaxis and treatment of systemic hypotension in an animal is provided. Most particularly, a method for treating hypotension caused by nitric oxide synthesis through administering a low or essentially arginine-free parenteral formulation to an animal, so as to reduce or eliminate nitric oxide synthesis is described. A method for treating an animal in septic shock is also disclosed, comprising administering to the animal an anti-hypotensive formulation comprising a mixture of amino acids, which is essentially arginine free. Prophylaxis or treatment of systemic hypotension, particularly that hypotension incident to chemotherapeutic treatment with biologic response modifiers, such as tumor necrosis factor or interleukin-1 or -2, may be accomplished through the administration of the defined anti-hypotensive formulations until physiologically acceptable systolic blood pressure levels are achieved in the animal. Treatment of an animal for septic shock induced by endotoxin may also be accomplished by administering to the animal the arginine-free formulations described.

9 Claims, No Drawings

OTHER PUBLICATIONS

Moncada, S., and Higgs, E. A., "Endogenous Nitric Oxide: Physiology, Pathology and Clinical Relevance," *European Journal of Clinical Investigation,* 21:361-374, 1991, published in Europe.

Nitric Oxide from L-Arginine," *Nature,* 333:664-666, 1988, published in Europe.

Old, Loyd J., "Tumor Necrosis Factor (TNF)," *Science,* 23:630-632, 1985, published in USA.

Yoshida and Kasama, "Biotransformation of Nitric Oxide," *Enviornmental Health Perspectives,* 78:201-206, 1987, published in USA.

Reif and Simmons, "Nitric Oxide Mediates Iron Release from Ferritin," *Archives of Biochemistry and Biophysics,* 283(2):537-541, 1990, published in USA.

Kruszyna et al., "Nitrite Conversion to Nitric Oxide in Red Cells and Its Stabilization as a Nitrosylated Valency Hybrid of Hemoglobin," *The Journal of Pharmacology and Experimental Therapeutics,* 241(1):307-313, 1987, published in USA.

Kosaka et al., "The Interaction Between Nitrogen Oxides and Hemoglobin and Endothelium-Derived Relaxing Factor," *Free Radical Biology and Medicine,* 7:653-658, 1989, published in USA.

Chevion et al., "Iron-Nitrosyl Bond configuration in Nitrosyl-Hemoproteins: A comparative EPR Study of Hemoglobin A and Hemoglobin Kansas," *Israel Journal of Chemistry,* 15:311-317, 1976, published in Israel.

Collier and Vallance, "Second Messenger Role for NO Widens to Nervous and Immune Systems," *Trends in Pharmacological Sciences Including Toxicological Sciences,* Elseview Science Publishers, Ltd., front page and pp. 428-431, 1989, published in United Kingdom.

Ignarro et al., "Endothelium-Derived Relaxing Factor Produced and Released from Artery and Vein is Nitric Oxide,"*Proc. Natl. Acad. Sci. USA,* 84:9265-9269, 1987, published in USA.

Murray et al., "Stabilization and Partial Characterization of Endothelium-Derived Relaxing Factor from Cultured Bovine Aortic Endothelial Cells," *Biochemical and Biophysical Research Communications,* 141(2):689-696, 1986, published in USA.

Marletta, Michael A., "Nitric Oxide: Biosynthesis and Biological Significance," name of publication unknown, Elseview Science Publishers, Ltd., pp. 448-493, 1989, published in United Kingdom.

Kilbourn et al., (1990), *Journal Nat'l Cancer Inst.,* 82(9):772-776.

Kilbourn et al., (May 1990), *Proc. Natl. Acad. Sci. USA,* 87:3629-32.

Martin et al., "Selective Blockade of Endothelium-Dependent and Glyceryl Trinitrate-Induced Relaxation by Hemoglobin and by Methylene Blue in the Rabbit Aorta," *The Journal of Pharmacology and Experimental Therapeutics,* 232(3):708-716, 1985, published in USA.

Buga et al., "Endothelium-Derived Nitric Oxide Relaxes Nonvascular Smooth Muscle," *European Journal of Pharmacology,* 161:61-72, 1989, published in Europe.

Stueher et al., "Synthesis of Nitrogen Oxides from L-Arginine by Macrophage Cytosol: Requirement for Inducible and Constitutive Components," *Biochemical and Biophysical Research Communications,* 161(2):420-426, 1989, published in USA.

Aisaka et al., "$N^G$ Methylarginine, An Inhibitor of Endothelium-Derived Nitric Oxide Synthesis, Is A Potent Pressor Agent in The Guinea Pig: Does Nitric Oxide Regulate Blood Pressure In Vivo?", *Biochemical and Biophysical Research Communications,* 160(2):881-886, 1989, published in USA.

Torti et al., "A Macrophage Factor Inhibits Adipocyte Gene Expression: An in Vitro Model of Cachexia," *Science,* 229:867-871, 1985, published in USA.

Kilbourn et al., "Activated Macrophages Secrete a Soluble Factor That Inhibits Mitochondrial Respiration of Tumor Cells," *The Journal of Immunology,* 133(5):2577-2588, 1984, published in USA.

Vallance et al., "Effects of Endothelium-Derived Nitric Oxide on Peripheral Arteriolar Tone in Man," *The Lancet, Ltd.,* 997-999, Oct. 1989, published in Europe.

Palmer et al., "Vascular Endothelial Cells Synthesize

Sakuma et al., (1988), *Proc. Natl. Acad. Sci. USA,* 85:8664-67.

Stuehr et al., (1989), *J. Exp. Med.,* 169:1011-20.

Hibbs et al., (1988), *Biochem. Biophys. Res. Comm.,* 157(1):87-94.

Stuehr et al., (1987), *J. Immunology,* 139:518-525.

Palmer et al., (1987), *Nature,* 327:542-526.

Natanson et al., (1989). *J. Exp. Med.,* 169:823-832.

Starnes et al., (1988), *J. Clin. Invest.,* 82(4):1321-25.

Nathan et al., (1990). *Journal Natl Cancer Inst. (USA),* 82(9):726-28.

Schmidt et al., (1988). *European J. of Pharmacology,* 154:213-216.

PARENTERAL FORMULATIONS FOR THE INHIBITION OF SYSTEMIC HYPOTENSION ASSOCIATED WITH NITRIC OXIDE PRODUCTION OR ENDOTHELIAL DERIVED RELAXING FACTOR

Work relating to the development of the present invention was supported at least in part by the National Institute of Health Grant No. DK-37116. Therefore, the Federal Government may have certain rights to use of this invention.

BACKGROUND OF THE INVENTION

1. Field of the Invention

The present invention relates to the field of prophylaxis and treatment of hypotension. Most particularly, the present invention proposes methods for the control and inhibition of hypotension or systemic shock through the administration of particularly defined formulations with limited nitric oxide-generating potential. The present invention also relates to specially tailored nutritional formulations for patients at risk of hypotension or systemic shock which include low concentrations of arginine or are arginine-free. Particular embodiments of the formulations also include ornithine or citrulline as urea cycle substrates. Anti-hypotensive TPN formulations for the general nutritional support of patients are also provided as within the scope of the present invention.

2. Background of the Art

Hypotension, or low blood pressure, is a complicating and often life-threatening condition attendant to shock, traumatic injury, sepsis, the administration of immunomodulators, as well as other situations. Thus, the risk of hypotension affects a significant number of persons throughout the world. For example, septic shock, a life-threatening complication of bacterial infections, affects 150,000 to 300,000 patients annually in the United States alone.[1]

The cardiovascular collapse and multiple metabolic derangements associated with septic shock are due largely to bacterial endotoxin (ET), which has been shown to elicit a septic shock-like condition when administered to animals[2]. ET is known to stimulate the synthesis and release of several cytokines and biological mediators having hypotensive activity; among the factors released, TNF, platelet activating factor (PAF), prostacyclin and complement-derived C5a anaphylatoxin have been proposed as contributors to the cardiovascular collapse of septic shock[3-6].

Although it has been shown that animals pretreated with anti-TNF antibodies[7], PAF receptor antagonists[8], and prostacyclin synthesis inhibitors[9] are significantly protected against septic shock, the relative importance of these mediators in the pathology of septic shock is presently uncertain.

There is also evidence that some of these mediators may act indirectly via release of secondary mediators. Thus, the finding that anti-TNF antibodies have little or no protective effect when given after ET exposure[7] suggests that TNF stimulates the production of another factor that is the actual hypotensive agent. Once initiated, synthesis and release of that factor can apparently continue even in the absence of detectable TNF. In 1980, Furchgott et al. (1980)[10] demonstrated that endothelial cells, which line blood vessels, can be stimulated to release a substance which relaxes vascular smooth muscle (i.e., causes vasodilatation). Since the chemical nature of this substance was completely unknown, it was simply named endothelium-derived relaxing factor (EDRF). It is hypothesized that many naturally-occurring substances which act as physiological vasodilators mediate all or part of their action by stimulating release of EDRF; these substances include, acetylcholine, histamine, bradykinin, leukotrienes, ADP, ATP, substance P, serotonin, thrombin and others.

The extremely short lifetime of EDRF (several seconds) hampered early efforts to chemically identify this molecule. In 1987, several laboratories suggested that EDRF may be nitric oxide (NO), which spontaneously decomposes to nitrate and nitrite. However, the fundamental problem in accepting this NO hypothesis was that mammalian systems were not known to contain an enzymatic pathway which could synthesize NO; additionally, a likely precursor for NO biosynthesis was unknown.

After observing that the arginine analog L-N$^G$-methylarginine (L-NNA) could inhibit vascular EDRF/NO synthesis induced by acetylcholine and histamine, and that EDRF/NO synthesis could be restored by adding excess L-arginine, certain of the present inventors proposed that arginine is the physiological precursor of EDRF/NO biosynthesis[11]. Certain of the present inventors later demonstrated that inhibition of EDRF/NO synthesis in the anesthetized guinea pig raises blood pressure.

The enzyme responsible for NO synthesis (nitric oxide synthase) has been partially characterized by some of the present inventors[14] and acts to oxidize a terminal nitrogen of the quanidino group of arginine, resulting in production of nitric oxide and citrulline. Macrophage-derived nitric oxide is now considered an important tumoricidal and bactericidal agent.

It has been reported that macrophage cells become "activated" by 12-36 hour after treatment with gamma-interferon, bacterial endotoxin and various cytokines in vitro. However, this in vitro "activation" system had been associated only with the initiation of tumor cell killing.

However, none of the literature or studies available prior to the present inventors work associated hypotension with nitric oxide, or the involvement of macrophages with hypotension.

Macrophages are a quantitatively insignificant component of normal blood vessel walls, and have never been shown to play any role in blood pressure regulation; i.e., there existed no biochemical, physiological or immunological data to suggest that macrophages had any role in pathological hypotension. Thus, the inventors sought to investigate the role of nitric oxide in systems relevant to the manifestation of hypotension, specifically the role of cytokine induced pathological hypotension, particularly on cells which comprise blood vessel walls.

Cytokines are well known to cause morphological and functional alterations in endothelial cells described as "endothelial cell activation". Distinct immune-mediators such as tumor necrosis factor (TNF), interleukin-1 (IL-1), and gamma-interferon (IFN) appear to induce different, but partially overlapping, patterns of endothelial cell activation including increased procoagulant activity[16], PGI2 production[17], HLA antigen expression[18] and lymphocyte adhesion molecule activation. Although these cytokines are reported to cause hypotension, vascular hemorrhage, and ischemia, the underlying mechanisms of altered vasoactivity are unclear[19,20].

In both clinical and animal studies on the effects of biological response modifiers[21,22], a major dose limiting toxicity has been hypotension and vascular leakage. The inventors have observed that endotoxin and tumor necrosis factor can induce over production of nitric oxide in animals.[23,24] Nitric oxide is a vasoactive substance which controls resting blood pressure.[12] This led the present inventors to postulate that hypotension in humans resulting from administration of biological response modifiers or from the development of overwhelming bacterial infections is due to excessive production of nitric oxide in sufficient concentration to relax vasoconstriction. However, macrophages are known to compose quantitatively only an insignificant component of normal blood vessel walls. Moreover, as a practical matter, it was unlikely that the amount of nitric oxide generated by circulating macrophages would be sufficient to elicit a "hypotensive" effect physiologically, as nitric oxide is not produced in vast enough quantities by the limited number of macrophages in blood vessel walls to produce such a pronounced physiological response. This, together with the recognized short half-life nitric oxide in vivo (3-5 seconds), diminished the theory that macrophage-derived nitric oxide was involved in hypotension.

The inventors also observed that nitric oxide is derived from the amino acid L-arginine.[11,25] L-arginine is a typical ingredient in commercially available TPN (total parenteral nutrition) formulations.

The inventors postulated that: 1) other cell types were possibly linked to pathological hypotension, such as those cells associated with blood vessel walls (endothelial cells); 2) vascular (e.g., endothelial) cells may be stimulated to produce NO by stimuli similar to those stimuli found to trigger NO generation by macrophage; and 3) septic shock (i.e., systemic vasodilatation induced by bacterial endotoxin) may result from massive activation of No biosynthesis by cells which are a quantitatively significant component of normal blood vessel walls.

As hypotension has been observed in patients maintained on standard TPN formulations, a potential valuable improvement in managing the risk of hypotension in these TPN-receiving patients is postulated by the inventors to be provided through a modified TPN formulation which reduces or eliminates the potential synthesis of nitric oxide. As the present inventors have observed that nitric oxide is derived from the amino acid arginine, the modification of a TPN formulation to reduce or eliminate the availability of arginine will reduce the production of nitric oxide and the hypotensive effects nitric oxide causes in patients receiving or producing endotoxin, or receiving tumor necrosis factor, or any other of a variety of biological response modifiers.

A TPN regimen of low or essentially arginine-free formulations is proposed by the inventors to reduce, if not eliminate, the risk of hypotension and septic shock in patients with bacterial infections. Clinical regimens which typically require the administration of a TPN formulation include, for example, nutritional support of cancer patients and others who have no or limited ability to tolerate oral feeding.

SUMMARY OF THE INVENTION

The present invention relates to methods and formulations for preventing or inhibiting systemic hypotension in an animal induced by a biological response modifier or by bacterial sepsis. By way of example, the biological response modifiers which are linked to causing systematic hypotension include the cytokines IFN, TNF, IL-1 and IL-2. The claimed method involves administering, preferably parenterally, an amount of a formulation which is arginine-free to a hypotensial or potentially hypotensive animal to reduce the level of serum arginine systemically, and thereby effect a reduction in the synthesis of nitric oxide.

The inventors have observed that nitric oxide is derived from the amino acid L-arginine. Therefore, the methods of the present invention include formulations having only very low concentrations of arginine or which are essentially arginine-free. Reduced arginine will serve to reduce nitric oxide synthesis and thus reduce the systemic hypotension manifest in an animal with an elevated levels of nitric oxide.

Particular embodiments of the TPN anti-hypotensive formulations include the addition of citrulline and/or ornithine. Citrulline and/or ornithine, which do not directly result in nitric oxide production, may be included to satisfy metabolic requirements such as those of the urea cycle, for example. As used in the present application, the term "low" arginine refers to a TPN solution which includes less than 0.1% arginine in the feeding solution (<100 mg. arginine/100 ml TPN). An even more preferred embodiment of the formulation includes a concentration of arginine between 0.1% and 0.001% arginine. Even more preferably, the anti-hypotensive TPN of the present invention includes about 0.001% (1 mg/100 ml TPN) arginine. In a most preferred embodiment of the present methods and formulations, arginine is included in the formulation at trace amounts of less than 0.1 mg/100 ml (about 0.0001%). The formulation in its most preferred embodiment is essentially arginine-free.

In a most preferred embodiment of the described methods, the formulation employed is an essentially arginine-free formulation and is also essentially ornithine-free and citrulline free. Alternatively, the essentially arginine-free formulation may include ornithine or citrulline. So formulated, the present methods also provide a specially tailored total parenteral nutrition (TPN) formulation for a patient at risk of systemic sepsis or suffering from other nitric oxide-mediated hypotension.

Although administration of the formulation to an animal is preferably parenteral, it is contemplated that other administration routes, such as by oral administration, for example, may prove useful as the method by which the essentially arginine-free or low arginine formulations may be used in the claimed method for inhibiting or preventing hypotension.

In one embodiment of the method, the arginine-free formulation is administered to an animal which may develop, is possibly developing, or is experiencing No-mediated systemic hypotension. The arginine-free formulations of the present inventive methods preferably include any pharmaceutically acceptable addition salts as commensurate with planned treatments.

A particular preferred use of the method of the present invention is in the prophylaxis or treatment of systemic hypotension manifest in a patient receiving chemotherapeutic agents, such as TNF, IL-2 (interleukin-2), IL-1 (interleukin-1), or a combination thereof. In this respect, the method involves administering to the patient, a nutritionally supportive amount of a low arginine or essentially arginine-free amino acid TPN formulation for a period of time until an elevation in the animal's systolic blood pressure to a physiologically acceptable level is demonstrated. By way of example, a physiologically acceptable systolic blood pressure level in an adult human is 100 mm Hg (100 millimeters of mercury) or greater. An adult human having a systolic blood pressure level of less than 100 mm Hg is defined as manifesting the condition known as "hypotension" for purposes of the methods of treatment defined herein. Most preferably, the formulation is prepared so as to be suitable for administration as a parenteral formulation to a patient.

An additional important application of the present invention is as a method for the treatment of septic shock, particularly that septic shock induced by bacterial endotoxin. Although prophylaxis is not practical here, treatment to improve and eliminate the condition is essential. The preferred method of treatment of septic shock according to the present invention therefore comprises maintaining the patient on an arginine-free or low arginine formulation comprising a mixture of amino acids until the patient demonstrates a maintained systolic blood pressure within physiologically acceptable levels. In an adult human, a physiologically acceptable systolic blood pressure is at least about 100 mm Hg (100 millimeters of mercury). Most preferably, the formulation is prepared so as to be suitable for administration as a parenteral formulation, and thus must be of a physiologically acceptable pH for administration parenterally.

Septic shock is a life-threatening condition that results from exposure to bacterial endotoxin. It is manifested by cardiovascular collapse and mediated by the release of cytokines such as for example TNF or IL-1.[36] The inventors have found that the administration of 40 $\mu$g/kg of bacterial endotoxin to dogs causes a 33% decrease in peripheral vascular resistance and a 54% fall in mean arterial blood pressure within 30 to 90 minutes. The inventors demonstrated a normalization of vascular resistance and systemic arterial pressure in a hypotensive animal within 1.5 minutes after intravenous administration of $N^G$-methyl-L-arginine (20 mg/kg). $N^G$-methyl-L-arginine is a potent and selective inhibitor of nitric oxide synthesis. Although $N^G$-methyl-L-arginine injection also increased blood pressure in control dogs, the hypertensive effect was much greater in endotoxemic dogs (24.8±4.7 mm Hg vs 47.8±6.8 mm Hg, n=4). $N^G$-methyl-L-arginine caused only a modest increase in blood pressure in control dogs made hypotensive by continuous intravenous infusion of nitroglycerin (17.1±5.0 mm Hg, n=3).

From these observations, the inventors propose, for the first time, a method for providing nutritional support and treating an animal including humans, in septic shock, at risk of developing septic shock, or having hypotension in a total parenteral formulation (TPN) which is essentially arginine-free. The inventors' observations reported herein regarding the correlation between serum arginine levels and blood pressure (See Examples 1 and 2), led to the development of a regimen of an essentially arginine-free or anti-hypotensive concentration of arginine in a mixture of amino acids in a formulation which may increase life-threatening, low blood pressure levels to physiological acceptable levels.

A reduction in serum arginine blood levels through the administration of such a formulation, thus reducing nitric oxide synthesis in vivo, is predicted by the inventors to provide an effective method of treating systemic shock and hypotension in an animal, including humans.

The inventors data also provides a proposed method by which hypotension may be inhibited or prevented by administering to a patient susceptible or at risk of developing hypotension, a formulation which is low in arginine (an anti-hypotensive concentration of arginine) or is essentially arginine-free. For purposes of the present application, a "low" concentration of arginine (an anti-hypotensive concentration of arginine) in the parenteral formation comprises less than 100 mg arginine/100 ml of formulation (0.1%). Even more preferably, a low concentration or an anti-hypotensive concentration of arginine comprises less than 0.0% arginine (10 mg/100 ml) of formulation. Still another preferred embodiment of the inventive method provides a formulation which includes 0.001% (or 1 mg/100 ml) or less arginine. Most preferably, the parenteral formulation includes 0.0001% arginine (0.1 mg/100 ml) or less.

Most preferably, this formulation is parenterally administered. In another embodiment, the formulation includes ornithine or citrulline in concentrations sufficient to meet physiological needs, such as urea acid cycle substrate requirements, of the patient where the parenteral formulation comprises the total nutritional support of the patient. The formulation should also be adjusted so as to be physiologically compatible for parenteral administration, such as to adjust the pH of the solution to be between 7.0 and 7.4.

When the formulation employed in the described method includes ornithine and/or citrulline, those concentrations of ornithine and citrulline most preferred to be included as part of the formulation are in the range of between about 1-2 g/l (or 0.10-0.20%) ornithine and/or 102 g/l (0.10-0.20%) of citrulline. The ornithine concentration most particularly preferred as part of the formulation is between 2-4 g/l of the TPN formulation in a patient-ready feeding formulation.

As used in the present application, a patient "at risk" for developing hypotension is defined as a patient who is receiving a regimen, or who is prescribed a regimen, of immunomodulators, such as, for example, tumor necrosis factor or interleukin-1 or -2, or who is suffering from systemic hypotension. Other patients at risk include patients with overwhelming bacterial infections or whom have been exposed to a bacterial endotoxin.

According to the presently disclosed methods for preventing hypotension in a patient, a patient would first be identified as "at risk" of hypotension. The identified person would then be administered a low-arginine or essentially arginine-free formulation which includes a mixture of amino acids in nutritionally supportive concentrations. Nutritionally supportive concentrations of amino acids as included within a parenteral formulation are provided at Table 3. The mixture of amino acids is ornithine-free and citrulline-free in one particularly preferred embodiment.

In still another embodiment of the present invention, the mixture of amino acids includes ornithine and citrulline in a concentration sufficient to meet physiological urea acid cycle substrate requirements of the patient. The formulation would be administered to the patient until a systolic blood pressure of physiologically acceptable levels is observed in the patient.

The "low" concentrations of arginine as defined for the present invention is between 0.001% and 0.1% arginine in a formulation ready to be administered to a patient (i.e. "patient ready"). The most preferred mode of administering the formulation to a patient is parenteral. Therefore, the most preferred embodiment of the described treatment formulation may be described as a total parenteral nutrition (TPN) formulation.

A mixture of particular essential and non-essential amino acids are included in the claimed anti-hypotensive formulations. A classification of amino acids recognized by those of skill in the art as "essential" or "non-essential" is provided in Lehninger et al.'s *Biochemistry* text,[26] and in Wagner[27]. These references are specifically incorporated herein by reference for this purpose.

Arginine is typically included in previously employed parenteral formulations commercially available. The concentration of arginine in standard formulations is about or greater than 0.4%. The present application presents a novel method of preventing/ controlling/inhibiting hypotension and treating septic shock through the limitation and/or exclusion of arginine as an ingredient in a TPN formulation. For example, the claimed formulations include in one particular embodiment, less than 0.1% arginine in a patient-ready formulation. The most preferred embodiment of the present invention employs an essentially arginine-free formulation which is also essentially ornithine-free and citrulline-free.

The involvement of arginine in hypotension and septic shock is demonstrated in the in vivo studies described herein. Studies conducted by the inventors also demonstrated that particular analogs of arginine (arginine antagonists) inhibit hypotension in vivo. The administration of particular arginine analog antagonists was thus found by the inventors to affect a variety of biochemical pathways physiologically, most notably by decreasing the production of nitric oxide.

The production of nitric oxide is proposed by the present inventors to be controllable through the limitation or elimination of available serum arginine in an animal. This goal of limiting or eliminating arginine in animal serum sufficient to reduce nitric oxide synthesis may most conveniently be accomplished through maintaining the animal on an arginine-free or low arginine nutritional regimen.

Because arginine is a typical ingredient in standard parenteral formulations and contributes as a urea cycle substrate, the parenteral formulation employed in the claimed methods in particular embodiments of the invention may include ornithine or citrulline. Ornithine and citrulline are known not to be direct precursors of NO, and are expected not to enhance or contribute to nitric oxide production or maintenance of nitric oxide levels. Ornithine or citrulline thus may be included as an effective urea cycle substrate to maintain physiological balance in the animal.

In a more general sense, the present invention may relate to a method for the prophylaxis or treatment of nitric oxide-induced systemic hypotension in a patient requiring total parenteral nutritional support. The necessity for maintaining a patient on a parenteral nutritional regimen occurs when a patient is unable to swallow, such as is typical of patients receiving chemotherapeutic agents which induce nausea, emesis or anorexia.

The arginine-free formulation is to be administered on an "as needed" basis, as determined by the attending physician until a sustained systolic blood pressure of at least 100 mm Hg is detectable in the patient. More specifically, and by way of example, the patient's systolic blood pressure should be monitored periodically until a systolic blood pressure of at least 100 mm Hg is recorded over at least a single 24 hour period.

While not intending to be limited to any particular theory or mechanism of action, it is postulated that the administration of an essentially arginine-free parenteral formulation will inhibit hypotension because such a reduction in serum-arginine levels will elicit a reduction in nitric oxide synthesis. Nitric oxide, as already discussed, has been observed by the inventors to constitute the vasoactive substance which causes hypotension in animals receiving biological response modifiers or endotoxin which causes septic shock. This theory is drawn from the inventors observations that patients receiving tumor necrosis factor also exhibit elevated blood nitric levels (a stable breakdown product of nitric oxide) when hypotension is manifest.

Arginine has been described as important in the urea cycle, and is thus important in overall patient health and disease. Therefore, a formulation with low or no arginine may be supplemented to maintain the overall health of the patient by including other nutritionally valuable ingredients. By way of example, the formulation may be supplemented by the inclusion of such nutritionally valuable ingredients as ornithine or citrulline, or both. Both ornithine and citrulline may be converted to arginine in the liver, and thus adequately sustain the urea cycle in a patient maintained on such formulation. Employing these methods and formulations, those persons who may have already lapsed into a state of septic shock, or who are already severely ill and being maintained on a respirator with total parenteral nutritional support, may be nutritionally supported without increasing the risk of exacerbating an already existing condition of septic shock or hypotension.

For purposes of the present inventive formulations and methods, the term "essentially arginine free" is defined as a final concentration of arginine of less than 0.0001% arginine by weight. A total volume of ready to feed TPN may be prepared by mixing 500 cc of a 2X concentrate of amino acids together with 55 cc of dextrose solution, most preferably containing minerals and vitamins.

Within this specification, the acronym "NO" will be understood to represent nitric oxide as well as any other additional vasoactive nitrogen oxides. Other abbreviations used in the drawings and other places in this application include the following.

ACh=acetylcholine
BAEC=bovine aortic endothelial cells
B.P.=blood pressure
CO=Cardiac output
EDRF=Endothelium-Derived Relaxing Factor
ET=endotoxin
GP=guinea pig
HIST=histamine
IFN=gamma-interferon
IV=Intravenous
L-Arg=L-arginine
LPS=lipopolysaccharide (endotoxin)
MBEC=murine brain endothelial cells
NO=Nitric Oxide
PAF=Platelet Activating Factor
PPS=Platelet - poor, plasma-derived serum
SAP=Systemic arterial pressure
SNP=sodium nitroprusside
SVR=Systemic vascular resistance TNF=Tumor Necrosis Factor
TPN=Total Parenteral Formulation

DESCRIPTION OF THE PREFERRED EMBODIMENTS

Clinical studies of biologic response modifiers such as certain cytokines have shown that a major dose-limiting toxicity associated with administration of such agents is hypotension. Nitrite, the predominant spontaneous oxidation product of No, is readily assayed and used herein for assays of NO production. Nitric oxide (NO) is a highly reactive compound which spontaneously decomposes to nitrate and nitrite in a culture medium.

The present invention involves implements the inventors' findings that IFN (100 U/ml) in combination with either TNF (500 U/ml), IL-1 (10 U/ml), or endotoxin (1 μg/ml.), can induce MBEC's to accumulate nitrite in a culture medium (15 to 80 μM) within 48 hours. TNF, IL-1 or endotoxin alone was found to induce the production of minimal levels of nitrites (1-3 μM).

The release of vasoactive factors such as NO by endothelial cells may play a role in the development of hypotension associated with the administration of these agents in vivo. This invention relates to a demonstration that cultured MBEC's produce NO in response to various combinations of cytokines and the potential role of NO in the pathophysiological causes of hypotension and cardiovascular collapse.

The present invention also relates to a method for inhibiting or preventing hypotension as well as septic shock through the reduction of nitric oxide synthesis. Most particularly, the method employs the administration of an arginine-free parenteral formulation to effect a reduction in serum arginine levels. This reduction in serum arginine levels is postulated to provide for a reduction in nitric oxide synthesis, as arginine is the substrate from which nitric oxide is formed. Nitric oxide has recently been demonstrated by the inventors to be derived from the amino acid L-arginine.[15]

As nitric oxide is a potent vasodilator linked to the development of hypotension and septic shock, the claimed methods propose the inhibition and prophylaxis of these conditions in an animal through the control of serum arginine concentrations and nitric oxide synthesis. The invention provides a reduction in nitric oxide synthesis by eliminating or limiting the arginine concentration in an animal's serum. A reduction in an animal's serum concentration of arginine is accomplished through restricting the amount of arginine given to the animal to not greater than about 0.1% arginine in a non-hypotensive TPN formulation.

Particular embodiments of the claimed formulations may include ornithine and citrulline, ornithine alone, or citrulline alone to supplement urea cycle substrate physiological requirements in the animal.

The present inventors have found that increased concentrations of nitrites were not associated with MBEC exposed to TNF and IFN in arginine-free culture medium. The nitrite concentration was found to increase in a dose dependent manner upon addition of L-arginine back to the medium of a culture of MBEC cells. The inventors have also found that nitrite accumulates when cultured mouse endothelial cells are exposed to immunomodulators and endotoxin[17].

For purposes of the present invention, the term "cytostatic" is defined as that physiological state of a cell characterized by a lack of active cell division. Thus, a culture or group of cells which are in a "cytostatic" state are not actively dividing or which are growth inhibited (i.e., virtually no cell growth).

The terms "anti-hypotensive" and "non-hypotensive" are used interchangeably in defining the present invention. These terms are intended to denote the nature of the formulation as limiting the onset of hypotension through decreased arginine concentrations and thus availability in the serum of arginine.

For purposes of the present invention, a "pressor" agent is defined as a pharmacological agent which causes an increase in blood pressure when administered to an animal. By way of example, phenylephrine is a "pressor" agent. However, other pressor agents would be expected to provide similar effects in the systems described herein. Other examples of pressor agents include dopamine, epinephrine, norepinephrine and phenylephrine.

The following examples are presented to describe the best mode, preferred embodiments and utilities of the present invention and are not meant to limit the present invention unless otherwise stated in the claims appended hereto. The following examples detail particular aspects and embodiments of the present invention:

EXAMPLE 1—Correlation Between Serum Arginine Levels And Blood Pressure

EXAMPLE 2—Correlation Between Plasma Arginine Levels And Response To Pressor Agents EXAMPLE 3—Anti-Hypotensive Arginine-free TPN formulation EXAMPLE 4—Anti-Hypotensive Formulation with Low Arginine EXAMPLE 5—Anti-Hypotensive Arginine-Free TPN Formulation PROPHETIC EXAMPLE 6—Formulations and Methods for Inhibiting Hypotension and Septic Shock

EXAMPLE 1

Correlation Between Serum Arginim Levels and Blood Pressure

The present example is provided to demonstrate the correlation between plasma arginine levels and blood pressure. More specifically, the present example demonstrates a correlation between low plasma arginine levels and increased blood pressure in endotoxin-treated animals.

The present example also demonstrates the utility for employing a parenteral formulation which is essentially arginine free or low enough in arginine to lower plasma arginine levels, to prevent or alleviate synthesis of nitric oxide. The onset of life-threatening levels of low blood pressure, such as that typically attendant to hypotension and septic shock would thus be prevented or alleviated in an animal.

The enzyme arginase was used to reduce plasma arginine levels in Spraque-Dawly rats (Weight per rat=250-300 gm). Arginase is an enzyme that irreversibly converts L-arginine to L-ornithine +urea. The rats were anesthetized with ethyl ether and then pithed as described Shiply and Tilden[30]. The animals were pithed prior to use in the present study so as to eliminate any neurological control of blood pressure.

Arginase was dissolved in sterile saline (1000 I.U./ml) and was administered by intravenous infusion at a rate of 300 I.U./min. for 20 min. One I.U. is the amount of arginase that converts 1 μmol of arginine to products per minute. Blood pressure was determined using a pressure transducer connected to an indwelling catheter placed in the carotid artery as described.[12]

Serum arginine concentrations,

The administration of arginase to pithed rats with or without exposure to endotoxin (15 mg/kg dose, ip), according to the dose outlined above, resulted in a decrease in plasma arginine levels of from 150 $\mu$M to $\leq 4$ $\mu$M within a few minutes. Plasma arginine remained at levels $\leq 4$ $\mu$M for at least 1 hour after the arginase infusion was stopped.

Blood pressure recording in the pithed rat.

To record blood pressure, a tracheotomy was first performed on each rat, after which the rats were artificially respired with room air. The left common carotid artery was then cannulated in each rat for blood pressure measurement via a Statham pressure transducer (Hato Rey, Puerto Rico) and displayed on a physiogram (Grass Instruments, Qunicy, Mass.). Heart rate was measured from the lead III electrocardiogram.

Two separate groups of animals were examined. The first group of animals, designated the "control" group, received no endotoxin. The blood pressure of the "control" group animals was measured at two different times, once before the administration of arginase and once after the administration of arginase.

The second group of animals, designated the endotoxin group, received a single dose of endotoxin of 15 mg/kg body weight, which was administered at least 6 hours prior to any subsequent arginase treatment. The blood pressure of all animals in both treatment groups was then measured at two different times, again once before arginase treatment and once after arginase treatment.

The results from this example are presented in Table 1.

TABLE 1

EFFECT OF REDUCED PLASMA ARGINASE ON BLOOD PRESSURE

| | No Arginase | | Arginase |
|---|---|---|---|
| | B.P. (mm Hg) | Average B.P. | B.P. (mm Hg) |
| Control Rats | | | |
| 1 | 61 | 59.8 ± 1.3 | 61 |
| 2 | 60 | | 60 |
| 3 | 60 | | 64 |
| 4 | 58 | | 68 |
| Endotoxin Rats (15 mg/Kg) | | | |
| 1 | 36 | 33.2 ± 3.3 | 44 |
| 2 | 34 | | 40 |
| 3 | 28 | | 28 |
| 4 | 32 | | 36 |
| 5 | 36 | | 44 |

Blood pressure readings for 4 control pithed rats were 61, 60, 60, and 58 mm Hg (average 59.8±1.3 mm Hg) (See Table 1). Following administration of arginase, blood pressure was unchanged in two rats and increased by 4 and 10 mm Hg in 2 other rats (average increase 3.5±4.7 mm Hg, not statistically significant).

Blood pressure readings for 5 rats at 6 hours after giving 15 mg/kg lipopolysaccharide (endotoxin) by intravenous injection was 36, 34, 28, 32, and 36 mm Hg (average 33.2±3.3 mm Hg, See Table 1). Note that the endotoxin-treated rats were clearly hypotensive relative to the controls.

Following administration of arginase, blood pressure in the endotoxin-treated rats increased by 8, 6, 0, 4, and 8 mm Hg (average increase 5.2±3.3 mm Hg). The average blood pressure increase following arginase treatment of the endotoxic, pithed rats was 15.7% (statistically significant, p<0.05).

Overall, this study shows that reducing plasma arginine levels has no significant effect on blood pressure in control animals, but did have a significant effect on blood pressure readings in endotoxic animals. The lack of a demonstrated effect in control animals may be due to the slow rate of NO formation in control animals, so as to negate any requirement for exogenous (i.e. plasma) arginine. Thus, a reduction in plasma arginine levels in such animals would not be a limiting factor for generating NO.

In contrast, the rate of NO formation in endotoxic animals is much faster than in control (non-endotoxic animals), and results in the development of hypotension. In these endotoxic animals, the cells making NO must obtain extra arginine from the plasma. When plasma arginine is very low in endotoxic animals (i.e. after arginase administration), there is not enough arginine available to sustain a pathologically high rate of NO synthesis by cells associated with blood vessel walls (i.e., endothelial cells). Thus, the concentration of NO is reduced, resulting in a concomitant reduction in the level of blood pressure reduction in the vasculature of the animal. Thus, depletion of serum arginine levels could be used to effect an increase in blood pressure in hypotensive animals.

Thus, use of arginine-free TPN solutions, or solutions sufficiently low in arginine concentration so as to effect a sufficient reduction in plasma arginine levels adequate to limit nitric oxide synthesis, for example, to about 4 $\mu$M arginine or less (i.e., 4 nM/ml serum arginine), are expected to have a beneficial effect comparable to that of arginase administration for preventing or treating hypotension, particularly hypotension in animals in septic shock.

EXAMPLE 2

Correlation Between Plasma Arginine Levels and Response to Pressor Agents

The present example is provided to demonstrate the correlation between low plasma arginine levels and increased response to "pressor" agents in vivo in endotoxin-treated animals. The particular "pressor" agent employed in this example is phenylephrine. However, virtually any "pressor" agent could be employed with equal utility to demonstrate the physiological effects disclosed by the present inventors. It has previously been observed that in septic shock, patients are hypotensive and no longer respond well to the usual pressor drugs such as phenylephrine. To determine if lowering plasma arginine would improve responsiveness, a second study was carried out in pithed rats.

Animals were pithed as described in Example 1. Blood pressure measurements were obtained also as described in Example 1. Arginase was also prepared according to the method described in Example 1.

Both left and right jugular veins were cannulated for drug administration; and left jugular was used for bolus administration of phenylephrine and the right jugular vein was used for continuous infusion of arginase. All animals from both groups (Control and Endotoxin) received phenylephrine in sequential doses of 0.3, 1.0, 2.0, or 6.0 ug/Kg.

The results from this example are presented in Table 2.

TABLE 2
EFFECT OF ARGINASE AND ENDOTOXIN ON BLOOD PRESSURE

| | Blood Pressure Increase (mm Hg) | | | |
|---|---|---|---|---|
| | Without Arginase | | With Arginase | |
| Phenylephrine dose | Raw Data | Ave. ± S.D. | Raw Data | Ave. ± S.D. |
| Study #1: Control Animals | | | | |
| 0.3 µg/Kg | +16,14,32,9 | 17.8 ± 5.0 | +4,9,20,10 | 13.3 ± 2.5 |
| 1.0 µg/Kg | +40,25,36,24 | 31.3 ± 4.0 | +12,17,40,21 | 22.5 ± 6.1 |
| 2.0 µg/Kg | +64,48,58,34 | 51.0 ± 6.6 | +28,30,66,31 | 38.8 ± 9.1 |
| 6.0 µg/Kg | +84,92,122,74 | 93.0 ± 10.3 | +64,72,120,63 | 79.8 ± 13.4 |
| Study #2: Endotoxic Animals | | | | |
| 0.3 µg/Kg | +2,0,4,2,3 | 2.2 ± 0.7 | +2,0,4,2,2 | 2.0 ± 0.6 |
| 1.0 µg/Kg | +6,4,9,10,6 | 7.0 ± 1.1 | +8,6,16,9,6 | 9.0 ± 1.8 |
| 2.0 µg/Kg | +12,10,24,12,10 | 13.6 ± 2.6 | +19,14,44,20,20 | 23.3 ± 5.3 |
| 6.0 µg/Kg | +25,26,72,26,20 | 33.7 ± 9.6 | +36,46,78,44,38 | 48.5 ± 7.6 |

This example shows the effects of endotoxin and of arginase on mean systolic blood pressure response to phenylephrine in pithed rats. Endotoxin (15 mg/kg body weight) was given by intravenous injection 6 hrs before the experiment began; arginase (300 I.U./Min. for 20 min.) was given intravenously to each rat after the "Without Arginase" measurements were made.

Table 2 shows the maximum increase in blood pressure following the phenylephrine dose indicated for each rat ("Raw Data"); note that the data is in pairs since each rat was tested first without arginase (at 0.3, 1.0, 2.0 and 6.0 ug/Kg phenylephrine, in sequence) and was then retested with phenylephrine in the same dose and sequence after arginase treatment. Thus, the first line of data in the Table shows that four control rats were each tested with 0.3 µg/Kg of phenylephrine. The first control rat showed a blood pressure of 16 mm Hg without arginase, but only 4 mm Hg after arginase administration ("with arginase"). For the second, third and fourth rats, the blood pressure increments were 14, 32 and 9 before arginase, respectively, and 9, 20 and 10 after arginase, respectively.

This data demonstrates that reducing plasma arginine levels through arginase treatment, enhances the "pressor" agent (such as phenylephrine), response in endotoxic animals, reducing the difference observed between endotoxic and control animal blood pressure increases at the same pressor agent dose. Moreover, endotoxic animals pretreated with arginase demonstrated an enhanced "pressor" effect (a statistically greater increase in blood pressure), compared to the pressor response observed in endotoxic animals receiving no arginase (See Table 2).

Endotoxin decreases an animals ability to present the normal hypertensive response (i.e., increase in blood pressure) to phenylephrine. Thus, compare the "Without Arginase" data of control and endotoxic rats at each dose of phenylephrine (Table 2). This effect occurs because the endotoxic animals are making large amounts of nitric oxide from arginine, and that causes hypotension and blunting of the response to phenylephrine.

Arginase administration improves the hypertensive response to a pressor agent, such as phenylephrine, dose. Smaller differences were observed between control and endotoxic animals given arginase (indicating only a small loss of responsiveness) relative to the larger differences between control and endotoxic animals not given arginase (indicating a large loss in responsiveness).

For example, at a phenylephrine dose of 6 µg/Kg, in animals not given arginase (i.e., having a higher serum arginine concentration), the pressor response to phenylephrine drops from 93.0±10.3 mm Hg (a pharmacologically useful pressor agent response) in control animals to 33.7±9.6 mm Hg (a poor pressor agent response) in endotoxic animals, a difference in pressor response of 59.3 mm Hg. In contrast, at the same phenylephrine dose in animals given arginase (i.e., decreased serum arginine levels), the pressor response in control and endotoxic animals was 79.8±13.4 and 48.5±7.6, respectively, a difference of only 31.3 mm Hg. Thus, depletion of plasma arginine with arginase very significantly restores the "normal" (hypertensive) response to pressor drugs, such as phenylephrine.

The data herein thus demonstrates that hypotension may be controlled, particularly in endotoxic animals, by manipulating an animal's serum arginine concentration. As serum arginine levels may be controlled in part through an animal's nutrition as they are through arginase administration, the present data provides a mechanism whereby hypotension (low blood pressure) may be corrected by maintaining the animal on a low/antihypotensive concentration or essentially arginine-free nutritional regimen. As such, the presently disclosed technique may also be used to prevent the development of hypotension in a patient at risk.

EXAMPLE 3

Anti-Hypotensive Arginine-Free TPN Formulation

The present example defines an anti-hypotensive TPN formulation of the present invention.

A sterile, non-pyrogenic, stable solution for parenteral administration to a patient having hypotension or at risk of hypotension or systemic shock, particularly those receiving immunomodulatory agents, is prepared from pure crystalline amino acids, which are dissolved in a glucose solution (5% to 20%) in the following concentrations to provide a 2X concentrate TPN or a ready-to-feed TPN formulation, as indicated:

TABLE 3

| Amino Acids | 2x concentration mg/100 ml formulation | Final Concentration (Feeding Formulation) g/l |
|---|---|---|
| isoleucine | 600–800 | 3–4 |
| leucine | 800–1200 | 4–6 |
| valine | 600–800 | 3–4 |
| phenylalanine | 200–400 | 1–2 |
| methionine | 200–400 | 1–2 |
| lysine | 600–800 | 3–4 |
| histidine | 200–400 | 1–2 |
| threonine | 400–600 | 2–3 |
| tryptophan | 100–300 | 0.5–1.5 |
| tyrosine | 50–150 | 0.25–0.75 |

TABLE 3-continued

| Amino Acids | 2x concentration mg/100 ml formulation | Final Concentration (Feeding Formulation) g/l |
|---|---|---|
| alanine | 800-1000 | 4-5 |
| aspartic acid | 400-600 | 2-3 |
| glycine | 800-1000 | 4-5 |
| proline | 600-800 | 3-4 |
| serine | 200-400 | 1-2 |

To obtain the preferred TPN formulation concentration suitable as a feeding formulation, a volume of 500 ml of the 2X concentrate (defined in Table 3) is mixed with 500 ml of a dextrose solution, for the production of 1 liter of the feeding formulation (i.e., 500 cc of a 2X concentrate of AA and 500 cc of dextrose solution). Most preferably, the dextrose solution is supplemented with a physiologically acceptable concentration of vitamins and minerals.

The TPN of the present methods may also include glutamic acid (400-600 mg/100 ml of a 2x conc., or 2-3 g/l in a final concentration) and/or taurine (50-100 mg/100 mls. of a 2-fold concentrate; 0.25-0.5 g/l final concentration).

The solution is then filter sterilized into appropriate containers for intravenous fluids. To prepare for administration, the volume is then brought to the desired feeding solution concentration with an equal volume of sterile glucose solution. The TPN as a ready to feed formulation is then to be kept cool. The solution may then be administered to a patient intravenously (I.V.). The pH of the TPN solution must also be adjusted to a physiologically acceptable pH, between 7.0 and 7.4. The formulation is arginine free.

EXAMPLE 4

Anti-Hypotensive Formulation with Low Arginine

If a formulation of amino acids for a patient having hypotension, or at risk of developing hypotension or septic shock, is desired which includes arginine, the formulation as outlined in Example 3 may be utilized after supplementation with arginine. Arginine will be added to constitute less than 0.1% final concentration by weight of the formulation (about 1 g. of arginine/liter of the TPN feeding formulation). The same amounts of the essential and non-essential amino acids (leucine, isoleucine, valine, phenylalanine, lysine, valine, isoleucine, threonine, tryptophan, histidine, lyrosine, alanine, glycine, proline and serine) as defined in Example 3 will be present; and the solution prepared in the same manner.

EXAMPLE 5

Anti-Hypotensive Arginine-Free TPN Formulation

If a formulation of amino acids for patients at risk of hypotension or septic shock, or receiving pharmacological agents which may cause such a condition, such as TNF (tumor necrosis factor), etc., is desired which is essentially arginine-free and contains ornithine and citrulline, the formula as outlined in Example 3 supplemented with ornithine and citrulline can be utilized.

Ornithine will then be added to constitute between about 1-2 grams ornithine per liter of the TPN feeding solution (between 0.1% and 0.2% by weight ornithine). Citrulline will be added to constitute about 1 gram citrulline per liter of the TPN feeding solution (about 0.1% by weight citrulline). The same amounts of the amino acids of Example 3 will be present, and the solution prepared in the same manner. The anti-hypotensive formulation is arginine free.

PROPHETIC EXAMPLE 6

Formulations and Methods for Inhibiting Hypotension and Septic Shock

The present prophetic example provides methods whereby the particularly defined arginine-free and low-arginine formulations of Examples 3-5 may be used in the treatment of patients at risk of developing hypotension and septic shock, or whom may require parenteral nutritional support and have already developed hypotension or septic shock.

The proposed formulations and proposed methods may be used most particularly in the clinical management of patients requiring total parenteral nutritional support and receiving immunomodulators. By way of example, the term "immunomodulator" refers to such agents as interferon, interleukin-2, and tumor necrosis factor.

Many of the class of substances recognized as immunomodulators are used as anti-cancer chemotherapeutic agents. Thus, it is envisioned that the presently described methods would be effective for the clinical management of patients being maintained on parenteral nutritional support and receiving chemotherapeutic agents with immunomodulatory action.

According to the present invention, a method for prophylaxis or treatment of systemic hypotension related to the elevated production of nitric oxide in an animal is provided comprising administering to the animal a non-hypotensive formulation comprising a mixture of amino acids in a pharmaceutically acceptable diluent. The formulation may be essentially arginine-free, in a most preferred embodiment of the method. A non-hypotensive formulation which includes a low arginine concentration may also be employed in another embodiment of the claimed method.

The formulation is to be administered to the patient until a physiologically acceptable blood pressure in the animal is reached and maintained. For a human, a physiologically acceptable systolic blood pressure level is about 100 mm Hg.

More particularly, the method of the present invention includes an essentially arginine-free or low arginine (between about 0.001% and about 0.1%) formulation comprising a mixture of amino acids. The formulation should be prepared so as to be physiologically suitable as an intravenous hyperalimentation (total parenteral nutrition) solution for patients requiring such solutions.

Stated as a range of concentrations for the most preferred mixture of amino acids, the formulation of the presently disclosed methods and specially tailored arginine-free formulations is defined in Table 4. Most preferably, the proposed concentrations to be included in such a formulation appear in Table 4.

TABLE 4

PREFERRED RANGES OF AMINO ACIDS
IN NON-HYPOTENSIVE FORMULATIONS about 3-4 g/l isoleucine (0.3-0.4%);
about 4-6 g/l leucine (0.4-0.6%);
about 3-4 g/l lysine (0.3-0.4%);
about 1-2 g/l methionine (0.1-0.2%);
about 1-2 g/l phenylalanine (0.2-0.2%);
about 2-3 g/l threonine (0.2-0.3%);
about 0.5-1.5 g/l tryptophan (0.05-0.15%);
about 3-4 g/l valine (0.3-0.4%);

TABLE 4-continued
PREFERRED RANGES OF AMINO ACIDS IN NON-HYPOTENSIVE FORMULATIONS about 4-5 g/l alanine (0.4-0.5%);
about 1-2 g/l histidine (0.1-0.2%);
about 3-4 g/l proline (0.3-0.4%);
about 1-2 g/l serine (0.1-0.2%);
about 0.25-0.75 g/l tyrosine (0.025-0.075%);
about 4-5 g/l glycine (0.4-0.5%); and
about 2-3 g/l aspartic acid (0.2-0.3%).

The formulation may also include ornithine. Where ornithine is part of the particular formulation, it is to be included at a concentration of about 1-2 grams/l of the TPN feeding formulation (about 0.1-0.2% ornithine).

Where the formulation is a parenteral formulation, the mixture should be adjusted so as to be physiologically compatible for parenteral administration.

The described non-hypotensive parenteral nutritional formulations may alternatively include low concentrations of arginine found not to provide sufficient substrate for nitric oxide production in hypotensive animals. A low concentration of arginine for purposes of the present invention is defined as less than or equal to about 0.1% arginine in the feeding formulation ready to be administered to the patient. Most preferably, the formulation may include between about 0.01% to about 0.1% arginine.

An additional most preferred embodiment of the claimed invention is essentially arginine free. In one particularly defined embodiment of the essentially arginine-free formulation, the amino acids ornithine and citrulline are included. Ornithine and citrulline contribute to the urea cycle substrate requirements of the animal. Where ornithine and citrulline are included in the formulation, the concentration of these ingredients most preferred comprise about 0.1-0.2% (or 1-2 g/l) ornithine and about 0.1% (or 1 g/l) citrulline.

TABLE 5
Arginine-Free Formulation Mixture of Amino Acids

| Amino Acid | 2X Concentrate (mg/100 ml) | Final Feeding Concentration (g/l) |
| --- | --- | --- |
| Isoleucine | 600 | 3 |
| Leucine | 1,000 | 5 |
| Lysine | 1,000 | 5 |
| Methionine | 200 | 1 |
| Phenylalanine | 300 | 1.5 |
| Threonine | 400 | 2 |
| Tryptophan | 200 | 1 |
| Valine | 500 | 2.5 |
| Alanine | 900 | 4.5 |
| Histidine | 300 | 1.5 |
| Proline | 700 | 3.5 |
| Serine | 400 | 2.0 |
| Tyrosine | 450 | 2.0 |
| Glycine | 800 | 4.0 |
| Aspartic acid | 600 | 3 |
| Ornithine | 400 | 2 |

The ornithine content described for the formulation above may be omitted and replaced with citrulline at a concentration of about 2 g/l. The amino acids concentrate (2X0 is mixed with a pharmaceutically acceptable diluent, such as for example, a glucose solution in a proportion of 1 to 1 (1 part amino acid solution to 1 part of a dextrose solution). In addition, trace elements, vitamin supplements and essential salts ($Na^+$, $K^+$, $PO_4^{--}$, $Ca^{++}$, $Mg^{++}$) may be added.

The anti-hypotensive formulations as part of a method for treating or preventing hypotension may be administered as a parenteral nutritional formulation according to parenteral feeding methods well known to those of skill in the medical arts.

In practicing the claimed method, a physiological benchmark will be referred to in reference to determining at what point the administration of the arginine-free formulation should be terminated. For example, the patient's systolic blood pressure level may be monitored so as to determine when the patient has reached a physiologically acceptable level. A return to normal systolic pressure may then be used to indicate the point at which nitric oxide production was being reduced, and had escaped risk of a greater reduction in peripheral vascular resistance or arterial blood pressure.

As generally defined according to the claimed method, hypotension (low blood pressure) is defined as an adult human systolic blood pressure level of less than about 100 mm Hg. A physiologically acceptable systolic blood pressure in an adult human is at least about 100 mm Hg systolic blood pressure.[40]

It has been observed that serum arginine levels increase upon the administration of a standard TPN formulation.[41] Therefore, by eliminating arginine as an ingredient in a TPN formulation, the inventors propose that serum arginine levels will be significantly reduced in patients receiving such an arginine-free TPN formulation as compared to similarly situated patients whom had instead been receiving a standard TPN solution. A standard TPN solution which includes greater than about 0.1% arginine would not be expected to constitute a hypotensive formulation.

Changes may be made in the following methods and formulations defined therein, without departing from the scope and spirit of the following claims.

Those of skill in the pharmaceutical and/or neurophysiological arts will be able to practice the present invention with the aid of the disclosure provided here, the following references may facilitate practice or enhanced understanding of certain aspects. Inclusion of a reference in this list is not intended to and does not constitute an admission that the reference constitutes prior art with respect to the present invention.

The following references are specifically incorporated herein by reference in pertinent part for the purposes indicated herein.

BIBLIOGRAPHY

1. Parrillo, J. E., (1989), Septic Shock in Humans: Clinical Evaluation, Pathogenesis, and Therapeutic Approach in: Textbook of Critical Care, 2nd ed.,
2. Natanson et al., (1989), J. Exp. Med., 169:823.
3. Halush Ka et al., (1985), Crit. Care Med., 13:451.
4. Smedegard et al., (1989), Am. J. Pathol., 135:489.
5. Buetler et al., (1985), Science, 229:869.
6. Casals-Stenzel, (1987), European. Pharmacology, 135:117.
7. Wise et al., (1985), Circ. Shock, 17:59.
8. Hana sawa et al., (1989), Surg. Gynecol. Obstet., 168:232.
9. Tracey et al., (1987), Nature, 330:662-664.
10. Furchgott et al., (1980), Nature, 288:373-376.
11. Sakuma et al., (1988), PNAS, 85:8664-8667.
12. Aisaka et al., (1989) BBRC, 160:881-886.
13. Stuehr et al., (1989), J. Exp. Med., 169:1011-1020.
14. Stuehr et al., (1989), BBRC, 161:420-426.
15. Wagner et al., (1983), PNAS, 80:4518-4521.
16. Bevilaqua, (1986), PNAS, 83:4533-5437.
17. Rossi, (1985), Science, 229:174.

18. Pober, (1987), J. Immunol., 138:2149-2154.
19. Goldblum et al., (1989), Infect. Immunol., 57:1218-1226.
20. Tracey et al., (1986), Science, 234:470.
21. Rosenberg et al., (1986), Clinical Res., 34(2):413A.
22. Dinarello et al., (1989), Progress in Clinical and Biological Res., 286:243-263.
23. Kilbourn et al., (1990), Proc. Natl. Acad. Sci., 87:3629-3632.
24. Kilbourn et al, (1990), B.B.R.C., 172:1132-1138.
25. Kilbourn, (1990), J.N.C.I., 82(9):792-796.
26. Lenninger et al., Eds., Biochemistxy, 2nd ed. (1975), Chpt. 25:693-723.
27. Wagner et al., (1983), PNAS, 80:4518-4521.
28. Tracey et al., (1986), Science, 234:470.
29. Cavender, (1987), J. Immunol., 138:2149-2154.
30. Shipley et al (1947), Proc. Soc. Exp. Biol. Med, 65:453-455.
31. Li et al, (1989), Chinese Medical Journal, 102:922-925.
32. Hesse et al., (1988), Surg. Gynecol. Obstet., 166:147.
33. Etienne et al., (1986), Pharmacol. Res. Commun., 18:71.
34. Salvemini et al., (1990), Proc. Natl. Acad. Sci., 87:2593.
35. Cecil's Textbook of Medicine, (1982), Cardiovascular Disease, Eds., pp. 155-168.
36. Vanzee et al., (1990), J. Immunol., 146:3478-3482.

What is claimed is:

1. A method for treating hypotension due to septic shock or cytokine-induced hypotension by reducing blood arginine concentrations in an animal comprising:
   selecting a hypotensive animal having a systolic blood pressure of less than 100 mm Hg;
   administering to said animal an anti-hypertensive parenteral formulation comprising an essentially arginine-free mixture of amino acids in an amount sufficient to reduce blood arginine concentrations;
   obtaining periodic blood pressure measurements of the animal; and
   continuing administration of the anti-hypotensive parenteral formulation until a systolic blood pressure of greater than 100 mm Hg is detected in the animal.

2. The method of claim 1 wherein the anti-hypotensive parenteral formulation comprises:
   about 1-2 g/l ornithine;
   about 3-4 g/l isoleucine;
   about 4-6 g/l leucine;
   about 3-4 g/l lysine
   about 1-2 g/l methionine;
   about 1-2 g/l phenylalanine;
   about 2-3 g/l threonine;
   about 0.5-1.5 g/l tryptophan;
   about 3-4 g/l valine;
   about 4-5 g/l alanine;
   about 1-2 g/l histidine;
   about 3-4 g/l proline;
   about 1-2 g/l serine;
   about 0.25-0.75 g/l tyrosine;
   about 4-5 g/l glycine; and
   about 2-3 g/l aspartic acid.

3. The method of claim 1 wherein the anti-hypotensive parenteral formulation comprises about 1-2 g/l ornithine or about 1 g/l citrulline.

4. A method for treating hypotension due to septic shock or cytokine-induced hypotension by reducing blood arginine concentrations in a patient comprising:
   selecting a patient with hypotension having an initial systolic blood pressure of less than 100 mm Hg;
   administering to the identified patient an arginine-free formulation comprising: about 3-4 g/l isoleucine; about 4-6 g/l leucine; about 3-4 g/l lysine; about 1-2 g/l methionine; about 1-2 g/l phenylalanine; about 2-3 g/l threonine; about 0.5-1.5 g/l tryptophan; about 3-4 g/l valine; about 4-5 g/l alanine; about 1-2 g/l histidine; about 3-4 g/l proline; about 1-2 g/l serine; about 0.25-0.75 g/l tyrosine; about 4-5 g/l glycine; and about 2-3 g/l aspartic acid, in an amount sufficient to reduce blood arginine concentrations; and
   making period systolic blood pressure measurements of the patient until a systolic blood pressure of at least 100 mm Hg is maintained for a period of time sufficient to establish a stable systolic blood pressure in the patient.

5. The method of claim 4 wherein stable systolic blood pressure is a systolic blood pressure of at least 100 mm Hg maintained for at least 24 hours.

6. The method of claim 4 wherein the anti-hypotension formulation includes ornithine and citrulline.

7. The method of claim 4 wherein the hypotension inhibiting formulation includes about 1 g/l citrulline and between 1-2 g/l ornithine.

8. The method of claim 4 wherein the hypotension is in response to tumor necrosis factor, interleukin-2, or interleukin-1.

9. The method of claim 1, 2, 3 or 4 wherein the patient is a human.

* * * * *

UNITED STATES PATENT AND TRADEMARK OFFICE
CERTIFICATE OF CORRECTION

PATENT NO. : 5,286,739

DATED : February 15, 1994

INVENTOR(S) : Robert G. Kilbourn, Owen W. Griffith and Steven S. Gross

It is certified that error appears in the above-identified patent and that said Letters Patent is hereby corrected as shown below:

```
In claim 4, column 20, line 33, delete the word "period" and
insert therefore --periodic--.
```

Signed and Sealed this

Second Day of August, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,286,739
DATED : February 15, 1994
INVENTOR(S) : Robert G. Kilbourn, et al It is certified that error appears in the above-indentified patent and that said Letters Patent is hereby corrected as shown below:

On the title page, item [73] Assignee: should read

-- Board of Regents, University of Texas System, Austin, Tx.

Cornell Research Foundation, Itahea, N.Y. --

Signed and Sealed this

Eighth Day of August, 1995

*Attest:*

BRUCE LEHMAN

*Attesting Officer*  *Commissioner of Patents and Trademarks*